(12) United States Patent

Ninni

(10) Patent No.: US 12,594,126 B2

(45) Date of Patent: Apr. 7, 2026

(54) INTRALUMINAL NAVIGATION USING VIRTUAL SATELLITE TARGETS

(71) Applicant: CANON U.S.A., INC., Melville, NY (US)

(72) Inventor: Brian Ninni, Woburn, MA (US)

(73) Assignee: Canon U.S.A., Inc., Melville, NY (US)

( * ) Notice: Subject to any disclaimer, the term of this patent is extended or adjusted under 35 U.S.C. 154(b) by 434 days.

(21) Appl. No.: 17/558,378

(22) Filed: Dec. 21, 2021

(65) Prior Publication Data

US 2022/0202273 A1 Jun. 30, 2022

Related U.S. Application Data

(60) Provisional application No. 63/152,081, filed on Feb. 22, 2021, provisional application No. 63/132,358, filed on Dec. 30, 2020.

(51) Int. Cl.
| | |
|---|---|
| *A61B 1/00* | (2006.01) |
| *A61B 34/00* | (2016.01) |
| *A61B 34/20* | (2016.01) |

(52) U.S. Cl.
CPC .............. *A61B 34/20* (2016.02); *A61B 34/71* (2016.02)

(58) Field of Classification Search
CPC . A61B 34/20; A61B 34/71; A61B 2034/2046; A61B 2034/2051;

(Continued)

(56) References Cited

U.S. PATENT DOCUMENTS

| | | | | |
|---|---|---|---|---|
| 9,827,115 | B2 * | 11/2017 | Walker | .................. A61B 90/36 |
| 2007/0135803 | A1 | 6/2007 | Belson | |

(Continued)

FOREIGN PATENT DOCUMENTS

| | | |
|---|---|---|
| JP | 2014-124218 A | 7/2014 |
| JP | 2016-529999 A | 9/2016 |
| KR | 10-2018-0100421 A | 9/2018 |

OTHER PUBLICATIONS

Wood, Bradford J. et al., "Navigation systems for ablation", Journal of Vascular and Interventional Radiology, Aug. 2010, pp. S257-S263 vol. 21, No. 8S.

*Primary Examiner* — Anh Tuan T Nguyen
*Assistant Examiner* — James Edward Boice
(74) *Attorney, Agent, or Firm* — Canon U.S.A., Inc., IP Division

(57) ABSTRACT

A system and method that provides navigation guidance for intraluminal procedures comprises: a catheter configured to be inserted into a lumen receive an actuating force from an actuator; and a tracking system configured to acquire position and orientation of the catheter with respect a lumen. A processor in communication with the actuator and the tracking system is configured to: register a position and/or orientation of the catheter tip with respect to a reference target, and generate one or more satellite targets in a region of interest surrounding the reference target. A display screen displays a virtual representation of the distal end of the catheter, and a virtual representation of the one or more satellite targets, as navigation guidance. A user is able to determine how to align the catheter tip with the one or more satellite targets to perform an intraluminal procedure.

21 Claims, 7 Drawing Sheets

(58) Field of Classification Search
CPC .... A61B 2034/2055; A61B 2034/2057; A61B
2034/2063; A61B 2034/2065; A61B
2017/22072; A61B 17/3417; A61B
2034/2068; A61B 2090/3983
USPC .......................................... 600/103; 604/264
See application file for complete search history.

(56)                    References Cited

U.S. PATENT DOCUMENTS

| | | | | |
|---|---|---|---|---|
| 2009/0171184 | A1* | 7/2009 | Jenkins .................. | A61B 34/10 |
| | | | | 606/130 |
| 2011/0295108 | A1* | 12/2011 | Cox ......................... | A61B 5/06 |
| | | | | 600/424 |
| 2011/0313288 | A1* | 12/2011 | Chi Sing .............. | A61B 8/0825 |
| | | | | 600/437 |
| 2012/0123205 | A1 | 5/2012 | Nie et al. | |
| 2012/0253200 | A1* | 10/2012 | Stolka .................... | A61B 1/041 |
| | | | | 600/459 |
| 2012/0289777 | A1* | 11/2012 | Chopra ................ | A61B 5/6852 |
| | | | | 382/128 |
| 2014/0258918 | A1* | 9/2014 | Morishima ........... | G06F 3/0481 |
| | | | | 715/790 |
| 2015/0142013 | A1* | 5/2015 | Tanner ................... | A61B 34/30 |
| | | | | 606/130 |
| 2015/0282887 | A1* | 10/2015 | Yamada ................ | G06T 19/003 |
| | | | | 600/425 |
| 2017/0086665 | A1 | 3/2017 | Klein et al. | |
| 2017/0251951 | A1 | 9/2017 | Hunter et al. | |
| 2017/0265952 | A1* | 9/2017 | Donhowe .............. | A61B 34/30 |
| 2019/0043215 | A1* | 2/2019 | Ito .......................... | A61B 34/20 |
| 2019/0175062 | A1 | 6/2019 | Rafii-Tari et al. | |
| 2019/0328349 | A1 | 10/2019 | Pereira et al. | |
| 2019/0380798 | A1* | 12/2019 | Itkowitz .............. | A61B 1/3132 |
| 2020/0054399 | A1 | 2/2020 | Duindam et al. | |
| 2020/0078101 | A1 | 3/2020 | Hunter et al. | |
| 2020/0078103 | A1 | 3/2020 | Duindam et al. | |
| 2020/0100855 | A1* | 4/2020 | Leparmentier ...... | A61B 1/3132 |
| 2020/0146588 | A1 | 5/2020 | Hunter et al. | |
| 2020/0367818 | A1 | 11/2020 | DaCosta et al. | |
| 2020/0375682 | A1 | 12/2020 | Kincaid et al. | |
| 2021/0338064 | A1* | 11/2021 | Fitterer ................... | A61B 1/05 |

* cited by examiner

FIG. 3

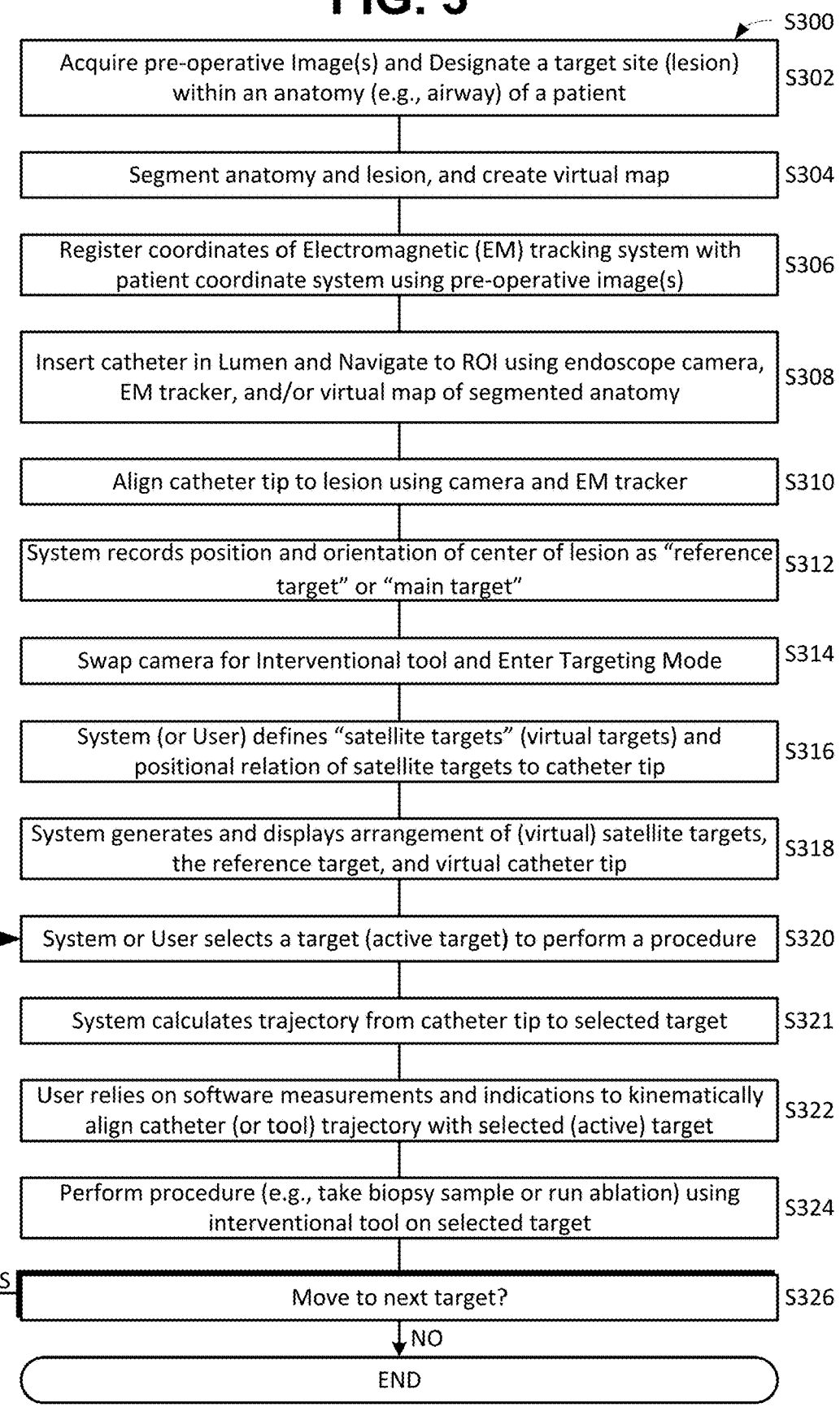

S300

| | |
|---|---|
| Acquire pre-operative Image(s) and Designate a target site (lesion) within an anatomy (e.g., airway) of a patient | S302 |
| Segment anatomy and lesion, and create virtual map | S304 |
| Register coordinates of Electromagnetic (EM) tracking system with patient coordinate system using pre-operative image(s) | S306 |
| Insert catheter in Lumen and Navigate to ROI using endoscope camera, EM tracker, and/or virtual map of segmented anatomy | S308 |
| Align catheter tip to lesion using camera and EM tracker | S310 |
| System records position and orientation of center of lesion as "reference target" or "main target" | S312 |
| Swap camera for Interventional tool and Enter Targeting Mode | S314 |
| System (or User) defines "satellite targets" (virtual targets) and positional relation of satellite targets to catheter tip | S316 |
| System generates and displays arrangement of (virtual) satellite targets, the reference target, and virtual catheter tip | S318 |
| System or User selects a target (active target) to perform a procedure | S320 |
| System calculates trajectory from catheter tip to selected target | S321 |
| User relies on software measurements and indications to kinematically align catheter (or tool) trajectory with selected (active) target | S322 |
| Perform procedure (e.g., take biopsy sample or run ablation) using interventional tool on selected target | S324 |
| Move to next target? | S326 |

YES

NO

END

INTRALUMINAL NAVIGATION USING VIRTUAL SATELLITE TARGETS

CROSS-REFERENCE TO RELATED APPLICATIONS

The present application claims priority to U.S. provisional applications No. 63/132,358 filed Dec. 30, 2020, and U.S. provisional applications No. 63/152,081 filed Feb. 22, 2021, the disclosures of which are hereby incorporated by reference in their entirety. Priority benefit is claimed under 35 U.S.C. § 119(e).

BACKGROUND INFORMATION

Field of Disclosure

The present disclosure relates to medical devices, systems, and methods. More particularly, the disclosure is directed to robot-assisted steerable medical devices configured for controlled intraluminal navigation using virtual satellite targets.

Description of Related Art

Steerable medical devices such as image-guided bronchoscopy instruments are known and available from many manufacturers, such Auris Health Inc., and Veran Medical Technologies Inc. These instruments have small cameras, a tracking system, and navigation software to assist the user with navigating the instrument to a target lesion, and preforming a procedure (e.g., taking a biopsy sample) on the target lesion. The navigation is performed using both an endoscopic camera and a positional tracking system, such as using an electromagnetic (EM) field sensor system. Examples of this technology are described in patent-related publications, such as pre-grant patent application publications US 20200146588, US 20200078101, US 20200367818, and US 20190175062. These publications are herein incorporated by reference for all purposes.

To improve treatment results, when using steerable medical devices as those described above, a physician might want to take multiple biopsy samples of a lesion, especially if the lesion is large. Similarly, for a tumorous lesion, an ablation procedure can be desirable to be carried out in multiple locations of the lesion. To that end, it is necessary that the procedure is carried out multiple times (e.g., multiple samples are taken from separate areas) on the same lesion, rather than resampling the same area multiple times. One reason for obtaining multiple samples is that, for example, cancerous tissue might be more prevalent in some parts of the lesion than others. Another reason for obtaining multiple samples from the same suspect lesion is that, for example, cancerous cells tend to spread to surrounding areas and the physician may want to determine the size of a tumor. In this regard, there is a challenge for steerable catheters with removable endoscope cameras, in that the physician is not able to visualize the lesion and the sites where earlier samples were taken. More specifically, in a steerable catheter with a removable imaging device, a physician may use the endoscope camera to align the catheter with an initial target location within a lesion, and then swap the camera for a biopsy tool to take a biopsy sample. However, to take additional biopsy samples, the physician must rely on positional tracking provided by the EM tracking system to reposition the catheter and take additional samples from locations (satellite targets) surrounding the initial target location. In this scenario, the physician may use pre-operative and/or intra-operative imaging techniques, such as Computed Tomography (CT), Magnetic Resonance Imaging (MRI), ultrasound (US) imaging, or other similar techniques to create a virtual representation of the procedure. However, even with image-guided techniques and robot-assisted technology, the physician's ability to safely acquire samples from satellite targets is limited due to the lack of accurate guidance or unexpected obstacles.

Image-guided techniques of the related art can assist the user with guiding the catheter to a lesion and aiming the catheter tip to a main target. However, the user is not assisted by image-guidance with taking samples at specific points around that main target. Therefore, there is a need for an improved navigation system which can provide real-time accurate navigation of a catheter to a main target location and successively navigate the same catheter to satellite target locations.

SUMMARY OF EXEMPLARY EMBODIMENTS

According to at least one embodiment of the present disclosure, a system for providing intraluminal navigation guidance in an intraluminal procedure, comprises: a catheter having a proximal section attachable to an actuator unit and a steerable section insertable into a lumen. The catheter has one or more than one tool channel, and is configured to receive an actuating force from the actuator unit to navigate the steerable section of the catheter through the lumen. The actuation force is transmitted from the actuator to the steerable section via one or more drive wires. A tracking system comprising at least one sensor is configured to establish a positional relation (position and orientation) between the catheter and a reference target located in a region of interest near a distal end of the catheter. A processor in communication with the actuator and with the at least one sensor, and a memory storing computer-executable instructions are configured to cause the processor to: determine, based on data from the at least one sensor, a position and orientation of a distal end of the steerable section of the catheter with respect to the reference target; generate one or more satellite targets surrounding the reference target; and display, on a display screen, one or more of (a) a virtual representation of the distal end of the steerable section, (b) an image the reference target, (c) a virtual representation of the one or more satellite targets, and (d) navigation guidance for successively aligning the distal section of the catheter with the reference target and with the one or more satellite targets.

According to one embodiment, the system is configured to have the software display virtual satellite targets surrounding the reference target. In one embodiment, displaying a virtual representation of the distal portion of the catheter and displaying a virtual representation of the satellite target should be enough for a user to be able to determine how to align with the catheter tip to the satellite targets. In other embodiments, additional features, such as calculating subsequent positions and/or orientations and/or trajectories of the distal portion of the catheter to successively align and/or navigate the distal portion of the catheter to each one of the satellite targets, and displaying such information can make the process more efficient, but are not essential for implementing the embodiment of a system that can assist the user with aligning the catheter tip to an 'active' satellite target, such that the user can cycle from one satellite target to the next. The system or the user can selectively activate the satellite targets one by one to successively align and/or guide the catheter tip to each satellite target. The software can also assist the user with aligning the catheter tip to the 'active' satellite target by changing the color or size of the active target, and the user can manually cycle from one satellite target to the next. Alternatively, the system can be configured to provide automatic guidance for cycling from one satellite target to the next in a predetermined order, for example, by detection of the sampling through one or more sensors.

The various embodiments of the present disclosure will assist the user with aiming at and taking samples from different locations within a lesion without removing the catheter from the lumen. This can reduce the time of the procedure, as well as increase the confidence in the sampling since the user can virtually track the positions of the sampling locations by following the satellite targets with respect to the reference target.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 3 illustrates a workflow process for intraluminal navigation and targeting using satellite targets to conduct an intraluminal procedure;

DETAILED DESCRIPTION OF EXEMPLARY EMBODIMENTS

Figure 1:
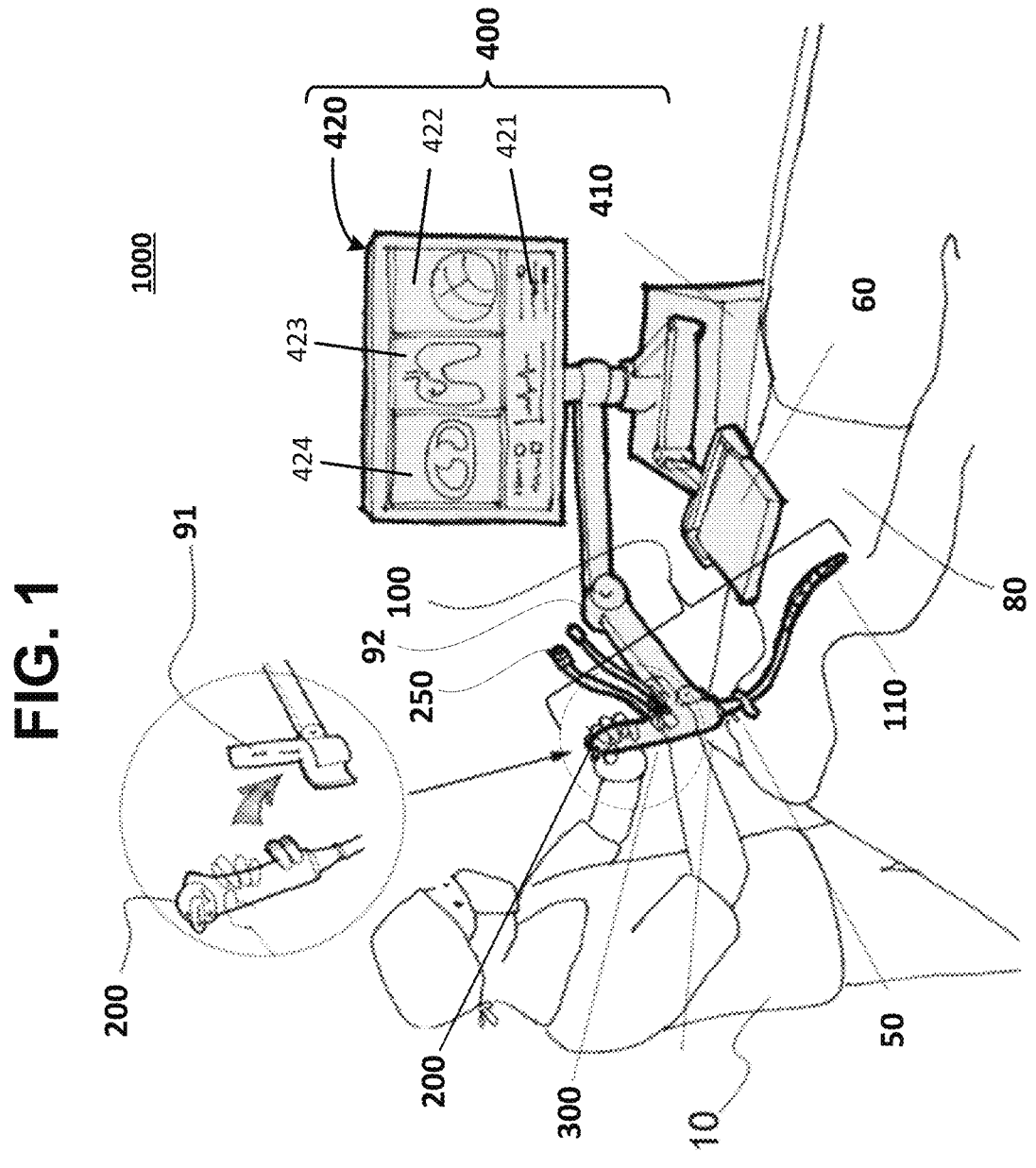
FIG. 1 illustrates an example embodiment of a robot-assisted endoscope system 1000 for intraluminal interventions in a medical environment, such as an operating room.

Before the various embodiments are described in further detail, it is to be understood that the present disclosure is not limited to any particular embodiment. It is also to be understood that the terminology used herein is for the purpose of describing exemplary embodiments only, and is not intended to be limiting.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where an analogous to "at least one of A, B, and C, etc." is used, in general such a construction is intended in the sense one having skill in the art would understand the recitation (e.g., "a system having at least one of A, B, and C" would include but not be limited to systems that have A alone, B alone, C alone, A and B together, A and C together, B and C together, and/or A, B, and C together, etc.). In those instances where an analogous to "at least one of A, B, or C, etc." is used, in general such a construction is intended in the sense one having skill in the art would understand the recitation (e.g., "a system having at least one of A, B, or C" would include, but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear.

The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the action and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

The present disclosure generally relates to medical devices, and it exemplifies embodiments of a robotic catheter. A particular example of a robotic catheter is a continuum or snake-like catheter, which may be equipped with an imaging device, such as a camera or an optical probe The embodiments of the robotic catheter and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

One or more embodiment of the present disclosure are directed systems, methods, and computer-readable media for robot-assisted steerable medical devices configured for controlled intraluminal navigation using virtual satellite targets. The term "intraluminal" shall be understood as "within a lumen" or inside a lumen.

<Endoscope System>

An exemplary configuration of a robot-assisted endoscope system 1000 is described with reference to FIG. 1 and FIG. 2A-2C. FIG. 1 illustrates an example representation of a medical environment such as an operating room where a robot-assisted endoscope system 1000 can be used. The robot-assisted endoscope system 1000 may include a steerable instrument 100 (a steerable medical device) operable by a user 10 (e.g., a physician) to perform an intraluminal procedure on a patient 80. The robot-assisted endoscope system 1000 may include a computer system 400 operatively connected to the steerable instrument 100 via a robotic platform 90. The robotic platform 90 includes a one or more robotic arms 92 and translation stage 91. The computer system 400 (e.g., a system console) includes a central processing unit (CPU) 410 comprised of one or more processor, and a display screen 420 such as a liquid crystal display (LCD), OLED or QLED display. A storage memory 411 (ROM and RAM memory), a system interface 412 (FPGA card), and a user interface 413 (e.g. mouse and keyboard) are operatively connected to the CPU 410 and to the display screen 420, as shown in FIG. 2A.

The steerable instrument 100 includes a handle 200 and a steerable catheter 110, which are removably connected to each other via a connector assembly 50. The steerable catheter 110 may also be referred to as a steerable catheter sheath or a steerable sheath configured to form continuous curves based on actuation principles known for continuum robots or snake-like robots. The handle 200 includes an actuator system 300 which receives electronic commands from computer system 400 to mechanically actuate the steerable catheter 110. The handle 200 is configured to be detachably mounted on the robotic platform 90 for robotically guiding the steerable catheter 110 towards a target site within the subject or patient 80. When the handle 200 is not mounted on the robotic platform 90, the handle 200 can be operated manually by the user to control the steerable catheter 110. For treating or examining the patient 80, the steerable instrument 100 may include one or more access ports 250 arranged on or around the handle 200. Access ports 250 are used to introduce end effectors, or to pass fluids to/from the patient 80. A tracking system (comprising an electromagnetic (EM) field generator 60 and one or more EM sensors 190 arranged on the steerable catheter 110) is used for tracking the position, shape, and/or orientation of the steerable catheter 110 while being inserted through a bodily lumen 81 towards a lesion 181. The lesion 181 is a region of interest in or around the lumen of the patient. The lesion 181 may include a main target 82 (e.g., center of a tumor) and secondary regions (satellite targets) surrounding the main target.

During an endoscopy procedure, the system's processor or CPU 410 is configured to perform operations based on computer-executable code pre-stored in the system's memory 411. The display screen 420 may include a graphical user interface (GUI) configured to display one or more of patient information 421, an endoscope image 422 (live view image), an intra-operative guiding image 423, and a pre-operative image 424 (e.g., a slice image) of the patient 80.

Figure 2A:
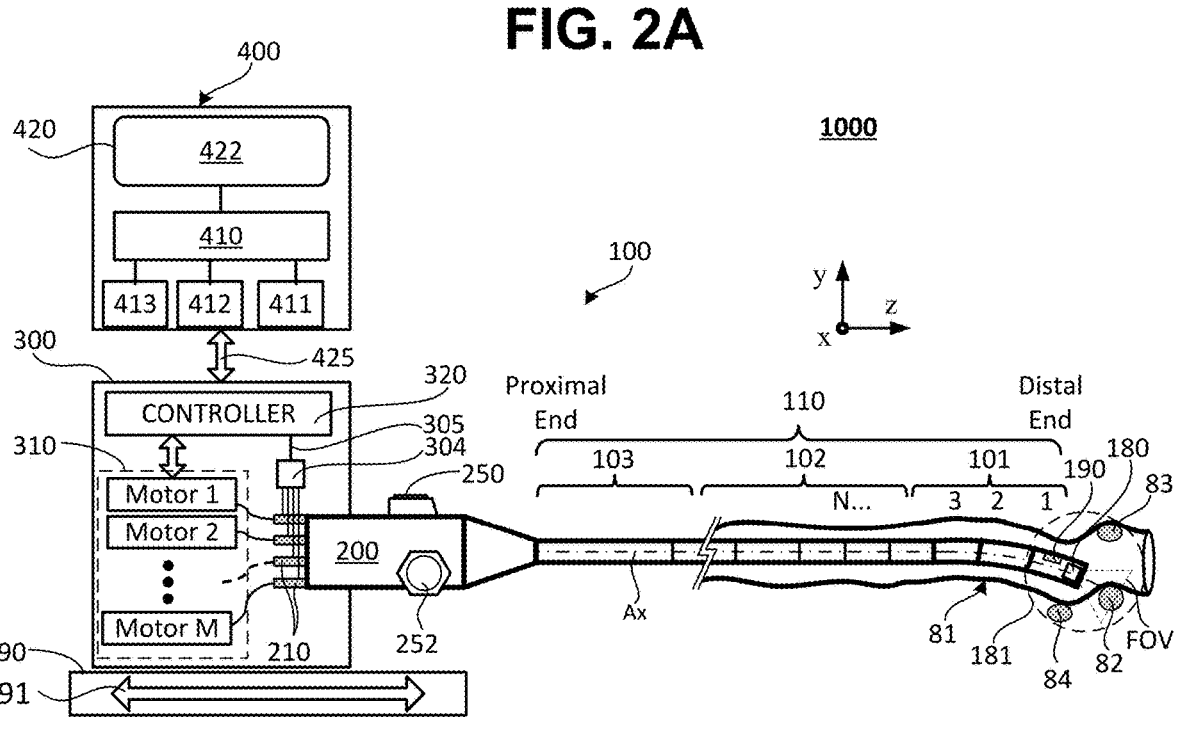
FIG. 2A illustrates an example embodiment of a robot-assisted endoscope system 1000 represented in functional block diagram.

FIG. 2A illustrates a general structure of the robot-assisted endoscope system 1000 in functional block diagram without the user and/or patient. As shown in FIG. 2A, the robot-assisted endoscope system 1000 includes a computer system 400 (e.g., a system console), a robotic actuator system 300, and a steerable instrument 100 which is connected to the actuator system 300 via a handle 200. The steerable instrument 100 includes the steerable catheter 110 which is comprised of a proximal section 103, a middle section 102, and a distal section 101 arranged in this order along a longitudinal axis (Ax). The proximal section 103 is a non-steerable section and serves to connect the steerable section to the handle 200 and to the actuator system 300. The middle section 102 and the distal section 101 constitute a steerable section of the steerable catheter 110; this steerable section is configured to be inserted into a bodily lumen 81 of the patient 80. The distal section 101 and middle section 102 are formed of a plurality of individually controllable segments 1, 2, 3 . . . N which are configured to be bent, curved, twisted, and/or rotated when advancing the steerable catheter through intraluminal tortuous paths of the bodily lumen 81. Each bending segment includes a plurality of ring-shaped components (rings). By convention, the steerable instrument 100 operates in a three-dimensional (3D) space defined by a 3D coordinate system of x, y, z Cartesian coordinates. The steerable catheter 110 includes at least one tool channel 105 which extends from the proximal end to the distal end along the longitudinal axis Ax. The steerable catheter 110 may include one or more position and/or orientation sensors 190 arranged along the length of the steerable catheter, and may include a removable imaging device 180. The imaging device 180 can include a fiber camera or a miniature electronic CMOS sensor arranged in the tool channel 105. The imaging device 180 is arranged such that its imaging plane is in the x-y plane, and the longitudinal axis Ax of the steerable catheter 110 extends along the z-axis of the 3D coordinate system.

For inserting an endoscope into a biological lumen 81 such as an airway of a patient 80, the tip (distal end) of the steerable catheter 110 is advanced (navigated) along a center line of the lumen. In this case, an imaging device 180 (e.g., a miniature camera) can be arranged in the tool channel 105 to provide a live-view image 422 of the lumen 81 taken directly from the instrument's field of view (FOV). However, in some embodiments, the steerable catheter 110 may not allow for the arrangement of a camera within the tool channel. In this case, navigation may be provided by intra-procedural guided imaging based on position and/or orientation provided by the one or more sensors 190 arranged along the sheath. In any case, in order to reach a desired target 82, the steerable catheter 110 must manipulated to bend, twist and/or rotate in different directions such that the distal section of the steerable catheter continuously changes shape and direction until it reaches an optimal location aligned with the target 82 such as a tumor.

The steering (bending, twisting, and/or rotating) of steerable catheter 110 is controlled by an actuation system comprised of the handle 200, the actuator system 300, the robotic platform 90 and/or a handheld controller (e.g., a gamepad with joystick), which are in communication with the computer system 400 via a network connection 425. The actuator system 300 includes a micro-controller 320 and an actuator unit 310 which are operatively connected to the computer system 400 via the network connection 425. The computer system 400 includes suitable software, firmware, and peripheral hardware operated by one or more processor of CPU 410. The computer system 400, the actuator system 300, and the handle 200 are operably connected to each other by the network connection 425 (e.g., a cable bundle or wireless link). In addition, the computer system 400, the actuator system 300 and the handle 200 are operatively connected to each other by the robot platform 90. In some embodiments, the actuator system 300 may include or be connected to a handheld controller, such as a gamepad controller or a portable computing device like a smart phone or a tablet. Among other functions, the computer system 400 and actuator system 300 can provide a surgeon or other operator with a graphical user interface (GUI) and patient information shown in the display screen 420 to operate the steerable instrument 100 according to a desired application.

Figure 2B:
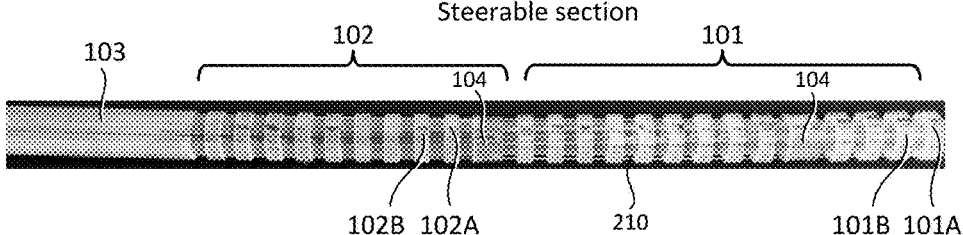
FIG. 2B illustrates an example embodiment of a multi-segment steerable catheter 110.

FIG. 2B shows an example embodiment of steerable catheter 110 which has its proximal section thereof configured to be attached to the handle 200. The bending segments of the steerable catheter 110 may be formed by ring-shaped components (e.g., ring 101A, ring 101B, etc.) arranged in the distal section 101, and ring-shaped components (e.g., ring 102A, ring 102B, etc.) arranged in the middle section 102. These ring-shaped components include a central opening which forms the tool channel 105, and plural conduits 106 (grooves, sub-channels, or thru-holes) arranged lengthwise equidistant from the central opening along the annular wall of each ring-shaped component. The non-steerable proximal section 103 is a tubular shaft made of extruded polymer material. The tubular shaft also has a central opening or tool channel 105, and plural conduits 106 surrounding the central opening. In this manner, at least one tool channel 105 inside the catheter 110 provides passage for imaging devices and/or interventional tools. Imaging devices may include an endoscope camera (videoscope) along with illumination optics (e.g., optical fibers or LEDs); the illumination optics emits illumination light to irradiate a lesion 181 which is a region of interest. The lesion 181 may include a main target 82 and sub-targets 83 and 84. The main target 82 and sub-targets 83-84 can be located along (inside) and/or around the bodily lumen 81 of patient 80.

Figure 2C:
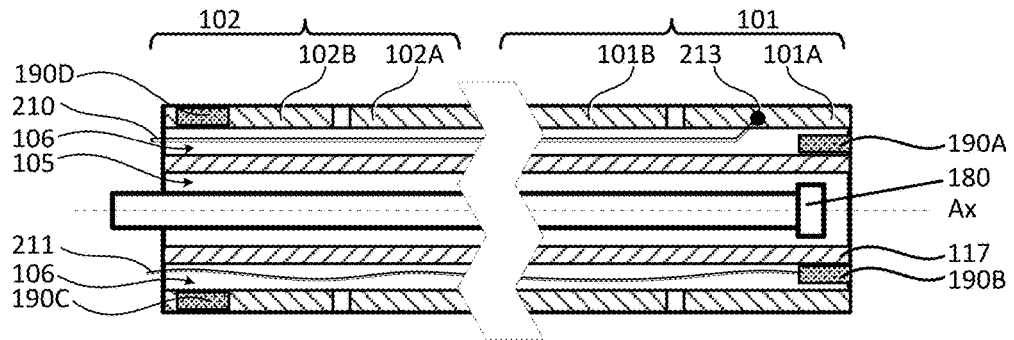
FIG. 2C illustrates a cross-sectional view of the steerable catheter 110 showing EM sensors 190, a tool channel 105, and wire conduits 106.

FIG. 2C illustrates a cross-sectional view taken in the lengthwise direction of the steerable catheter 110. Along its length, the steerable catheter 110 includes one or more EM sensors 190 (preferable two or more) and wire conduits 106 surrounding the tool channel 105. An inner sheath 117 is provided to facilitate passage of interventional surgical tools (end effectors) through the tool channel 105 without getting stuck inside the sheath. The distal section 101 of the steerable catheter 110 may contain at the distal end thereof, among other things, one or more sensors 190 fixedly attached to the wall of the catheter 110. In the embodiment shown in FIG. 2C, the distal section 101 includes a first sensor 190A and a second sensor 190B arranged inside wire conduits 106 in the wall of the ring-shaped components (e.g., ring 10A) at the distal end of the catheter 110. One or more additional sensors can be arranged at any other convenient location of the sheath. For example, as shown in FIG. 2B, the steerable section includes the distal section 101 formed by a plurality of ring-shaped components (rings 101A, 101B, etc.) and the middle section 102 formed by plurality of ring-shaped components (rings 102A, 102B, etc.). The steerable section is bendable in one or more directions at inflection points 104 by an actuation force (push or pull force) applied to one or more drive wires 210. Therefore, the one or more additional sensors can be provided in the middle section 102 and/or at the inflection points 104 to track the location and shape of the catheter 110 during navigation. In FIG. 2C, two additional sensors 190C and 190D are provided in the middle section 102 on the outer surface of ring 102B. As long as the sensors 190 can provide accurate information to map a posture and/or positional relation between the steerable catheter 110 and a main target 82, the arrangement of these sensors is not limited to any specific location or type of sensor.

In one embodiment, the sensors 190 are EM coils part of an EM tracking system configured to map the operation of the robotic controller 320 (e.g., a gamepad controller or handle 200) with the shape, position, and/or orientation of the steerable catheter 110. For example, a plurality of EM tracking sensors each with 6 Degrees of Freedom (6DOF) can be used to detect movement and calculate an amount of the twist, bend, and/or rotation of the middle and distal sections of the catheter 110 independently from each other. One or more sensors (e.g., a first sensor 190A and a second sensor 190B) can detect and track the position and orientation of the sheath's distal tip with respect to the main target. One or more additional sensors 190C and 190D may detect and track any changes in shape (bending) or deformation (ovalization) of the middle section of the sheath. A typical 6DOF EM sensor with a sub-millimeter diameter and about 5 mm length can measure both position and orientation. Therefore, a first pair of EM sensors (e.g., sensor 190A and sensor 190B) can measure position and rotation of the distal end of the sheath with respect to the main target, and an additional EM sensor 190C can measure the movement (bend, twist, rotation, etc.) of the middle section of the steerable catheter 110. In this manner, the signals of these EM sensors can be used by the controller 320 or system processor or CPU 410 to accurately track any changes in shape, position, and/or orientation of the various sections of catheter 110, and of the distal end of the sheath independently from each other. In other embodiments, the one or more sensors 190 may comprise radiopaque markers that are visible via fluoroscopic imaging, and/or patterns that are detectable via ultrasound imaging.

The controller 320 can control each drive wire 210 by actively driving an actuator or motor (310), sensing by a sensor (304 or 190), and operating according a feedback signal 305 to implement appropriate shaft guidance for navigating through tortuous intraluminal paths of the patient's anatomy.

Drive wires 210 are passed through one or more of wire conduits 106 along the wall of the ring-shaped components. The distal end of drive wires 210 are fixedly attached to the sheath at various points along the steerable section. For example, in FIG. 2C, a drive wire 210 is attached to the most distal ring 101A at an anchoring point 213. Other drive wires 210 are attached in a similar manner to inflection points 104. The wire conduits 106 also serve to pass therethrough other types of wires. For example, as shown in FIG. 2C, the conduits 106 serve to pass electrical cables 211 used to connect sensors 190 to the actuator system or computer system.

Referring back to FIG. 2A, the handle 200 provides an electromechanical interface between the steerable instrument 100 and the robotic actuator system 300 and/or the robotic platform 90. For example the handle 200 may provide an interface for mechanical, electrical, and/or optical connections, and a data/digital connection for interfacing the steerable catheter 110 with the actuator system 300 and/or computer system 400. The handle 200 may also provide one or more input ports 250 that a surgeon or operator can use to insert end effector tools through the tool channel 105. The handle 200 may also include one or more dials 252 for manual steering of the distal section 101 of the catheter 110. The term "end effector" refers to a working part of a surgical tool. Endoscopic surgical tools may include clamps, graspers, scissors, staplers, ablation needles, and other similar tools, which serve to manipulate body parts (organs or tumorous tissue) during examination or surgery, as it is known to those of ordinary skill in the art.

The robotic actuator system 300 includes an actuator unit 310 and a microcontroller 320. The actuator unit 310 may include a plurality of actuating motors (or actuators), which are shown as Motor 1 through Motor M, where M is an integer greater than one and equal to a number of drive wires 210 necessary for steering the various segments of the steerable catheter 110. The drive wires 210 are anchored at various points along the steerable section of the catheter 110. The robotic actuator system 300 also includes one or more sensors 304. Sensors 304 can include a strain sensor and/or a displacement sensor (e.g., a Hall-effect sensor) which serve to detect and/or measure compressive or tensile forces exerted by a push or pull force applied by the actuator unit to the drive wires 210. The sensors 304 can output a feedback signal 305 corresponding to the amount of compressive or tensile force (an amount of strain) being applied to each drive wire 210 while operating (steering) the steerable catheter 110. The signals 305 from the sensors 304 for each drive wire 210 are fed into the microcontroller 320 to control each actuator or motor individually. In this manner, each drive wire 210 can be actively controlled to implement appropriate guidance for navigating the steerable catheter 110 through intraluminal tortuous paths of a patient's anatomy.

In one example, when using a guidance system, the steerable catheter 110 is robotically advanced through a lumen 81 while sensors (304 and/or 190) measure the insertion depth of the catheter tip and the angulations of the steerable sections to obtain insertion trajectory information. The trajectory information is stored in a memory of the system and continuously updated as the steerable instrument is manipulated inside the lumen 81. After a short advance in insertion distance, the shape of the steerable catheter is corrected by adjusting (twisting and/or bending) segments of the instrument in such a way that the new shape closely matches the desired trajectory. This process is repeated until a target area is reached. The same process can be applied when the steerable instrument is withdrawn from the patient. This is analogous to known navigation techniques, e.g., as described in US 2007/0135803, which is incorporated by reference herein for all purposes.

Referring back to FIG. 1, for a catheter sheath with a removable imaging device (or catheters without an imaging device), the physician must rely on the EM tracking system to complete the endoscopy procedure. For example, to take a biopsy sample from within a lesion 181, the catheter 110 is robotically navigated through the lumen 81 towards the target 82 using an imaging device (e.g., an endoscope camera) to visualize the insertion path and to visually align the catheter to target. After the catheter tip is aligned with the target 82, the camera is removed from the catheter and swapped for a tool (e.g., a biopsy tool, an ablation needle, or other end effector). The system assists the user (a physician) in performing a predefined intraluminal procedure with the inserted tool (e.g., the physician acquires a biopsy sample). However, when the physician needs to take additional samples at satellite locations surrounding the target 82, there is a risk that the biopsy tool may deviate excessively from the region of interest or the biopsy tool may encounter obstacles.

As discussed above, to improve treatment results, when using steerable medical devices as the steerable catheter 110, a physician might want to take multiple samples or examine multiple locations of a patient's anatomy. Therefore, in a situation as shown in FIG. 2A, the distal end of the catheter 110 (catheter tip) can be also navigated to satellite targets including, e.g., a first satellite target 83, a second satellite target 84, and so on. In this case, the FOV of the imaging device 180 is available to identify and image the initial target 82, but after the imaging device 180 is swapped for an interventional tool (e.g., a biopsy tool), the imaging device 180 is no longer available to see the satellite targets 83 and 84. Accordingly, the endoscope system according to the present disclosure is configured to display the satellite targets in a virtual view, and present the virtual images of satellite targets in the display screen 420 with measurements and navigation instructions (navigation guidance) to assist the user in accurately navigating the steerable catheter 110 to the satellite targets without an endoscope camera.

<Robot-Assisted Navigation and Targeting Using Virtual Satellite Targets>

According to one or more embodiments of the present disclosure, the software system sets the initial target location as a "reference target" or "main target", and then the system generates and display virtual satellite targets surrounding the initial (reference) target. The system generates the satellite targets based on one or more parameters, such as the size of the lesion, the type of procedure, possible trajectories from the catheter to the satellite targets, etc. In this manner the system can assist the user with aligning the catheter tip to each satellite target, by defining one satellite target at a time as an "active" satellite target, and instructing the user to cycle from one satellite target to the next. This cycling from one target to the next can be done manually at the user's discretion, or it can also be performed automatically, for example in a biopsy procedure, by detection of the sampling size or depth through sensors (EM sensors, shape sensors, force sensors, etc.).

An example workflow process implemented by the computer system 400 is illustrated in FIG. 3. FIG. 3 is a workflow process S300 for how the user can use the satellite targets while taking biopsy samples within lesion 181. The user begins by segmenting the patient's anatomy (e.g., an airway) and suspected lesions therein, based on pre-acquired (pre-operative) volumetric image data, such as CT, MRI, ultrasound, fluoroscopy, or similar volumetric image data. Next, the user can register the EM coordinate system with the patient coordinate system to be able to virtually show the location of the catheter within the segmentation. The user then navigates the catheter to, and aligns the tip of the catheter with, a target (preferably the center of a suspected lesion). The user then enters a targeting mode and defines the position of one or more satellite targets. The satellite target positions can be pre-defined within the segmented lesion during the segmentation process. The software will then "place" the satellite targets around the center of the lesion (main target or reference target). The user can then cycle through the satellite targets to aim at (align), and the software system will instruct the user on how to successively align the catheter tip with each active satellite target before taking a biopsy sample.

More specifically, the workflow process S300 of FIG. 3 includes the following steps which are not necessarily in a chronological order. At step S302: the user controls the system to acquire pre-operative volumetric image(s) of a patient's anatomy. In some embodiments, the pre-operative images can be acquired from a picture archiving and communication system (PACS) server using the Digital Imaging and Communications in Medicine (DICOM) standard data interchange protocol. In some embodiments, volumetric image(s) of a patient's anatomy can be acquired at the time of the intraluminal procedure. At step S304: the system segments the acquired volumetric images to identify a region of interest (e.g., a patient's airway can be the anatomy and a suspected lesion therein can be a region of interest). From the segmentation process, the system creates a virtual map of the patient's anatomy and the region of interest.

At step S306: the computer system registers the coordinates of the electromagnetic (EM) tracking system with the patient coordinate system. Registration of the EM tracking system coordinates to the patient coordinate system is needed because the reference target is identified in the patient coordinate system. Registration techniques are well known to those skilled in the art, and such registrations are not limited to EM tracking. Nevertheless, EM tracking systems are increasingly used for real-time tracking of medical instruments because EM sensors are very small in size and have no restriction of line-of-sight (LOS). In that regard, referring back to FIG. 1, it should be recalled that electromagnetic (EM) field generator 60 interacts with one or more EM sensors 190 arranged on the steerable catheter 110 for tracking the position, shape, and/or orientation of the steerable catheter 110 while being inserted through a bodily lumen 81 towards a main target 82 (e.g., center of a tumor) within the patient 80. In addition, during the medical procedure, the dynamic navigation of the catheter tip or other instrument or component thereof to the targeted anatomy can be continuously tracked from the location(s) of one or more EM sensor (e.g., an electromagnetic coil sensor) incorporated within the catheter, and those locations can be represented as an image (moving image) of the catheter superimposed on slice image(s). The image(s) of the catheter can then be used to provide real-time image guidance of the catheter location relative to the main target 82 and one or more satellite targets.

At step S308: the system prompts the user to navigate the catheter sheath (steerable instrument) to the lesion in Navigation Mode using the endoscope camera, EM tracking system, and segmented airway view. At step S310: the user aligns the catheter tip with the target lesion (e.g., center of target lesion) using the endoscope camera and EM tracker. At step S312: the software system records position and orientation of the target lesion (target 82) as "reference target" or "main target". Here, the system can optionally record one or more images of the reference target; the one or more images can be subsequently used generate and place the satellite targets around the reference target. At step S314: the user swaps the endoscope camera for an interventional tool, and the system enters a Targeting Mode. In targeting mode, at step S314, the system may prompt the user to confirm location of the reference target before swapping the endoscope camera for the interventional tool. At step S316: the user defines "satellite targets" and possible alignment of satellite targets to catheter tip. In some embodiments, the software system can be programmed to automatically define satellite targets, for example, based on the size of the lesion (determined during the segmentation process). At step S318: the software system generates and displays the satellite targets surrounding the initial reference target. As this step, the reference target can be displayed as a virtual image representing the shape and/or size of the target lesion, or the system can display an actual image of the reference target. In addition, with the interventional tool inserted, the system can calculate and record the position and orientation of the catheter tip with respect to each of the satellite targets. Once the reference target and the satellite targets are defined and displayed, the system enters a Sampling Mode.

In the sampling mode, at step at S320: the user selects a target to perform a procedure (e.g., take a biopsy sample from). At step S321, the software system uses the position information from the EM tracking system and the position of the selected target to compute (calculate) the actions to be taken so that the catheter tip 1310 is appropriately aligned with and/or navigated to the selected (active) target. Since the catheter and/or the target may not be steady during a procedure, the software is constantly calculating the deviation between the catheter tip 1310 and the "active target". In calculating the deviation, the software system can use the position and/or orientation of the reference target recorded at step S314 and the positional information received from the tracking system. Using the information recorded at step S314, the software system calculates and displays the actual distance (position) and/or angle (orientation) for the trajectory in which the catheter tip 1310 should be actuated to reach the selected target. This is true regardless of whether the target to be sampled is the reference target 82 or any satellite target thereof. In other words, in the Sampling Mode, the system requires the same level of computation regardless of if the active target is a satellite or reference target. At step S322: the user or system, use the software measurements and indications to align the catheter trajectory with the selected target. The process of step S322 can include the guiding of the interventional tool (end effector) from the catheter tip to the selected target. At step S324: the user or system performs the desired procedure (e.g., takes biopsy sample or conducts ablation) on the selected target. At step S326: the system prompts the user (or automatically determines) whether more targets exist or whether additional operations are necessary. For example, after the selected target is sampled, the system outputs a prompt to the user to decide whether to "move to a next target" or end the procedure. Alternatively or additionally, at step S326, the system can prompt the user to evaluate whether the procedure was successful, or the system can warn the user about an incomplete or unsuccessful procedure. Steps S320 to S326 can be iteratively repeated until all successively selected targets are processed (sampled, ablated, etc.). When all targets are treated, the process of FIG. 3 ends (e.g., the catheter is withdrawn from the patient).

<Robot Assisted Alignment Guidance>

Figure 4:
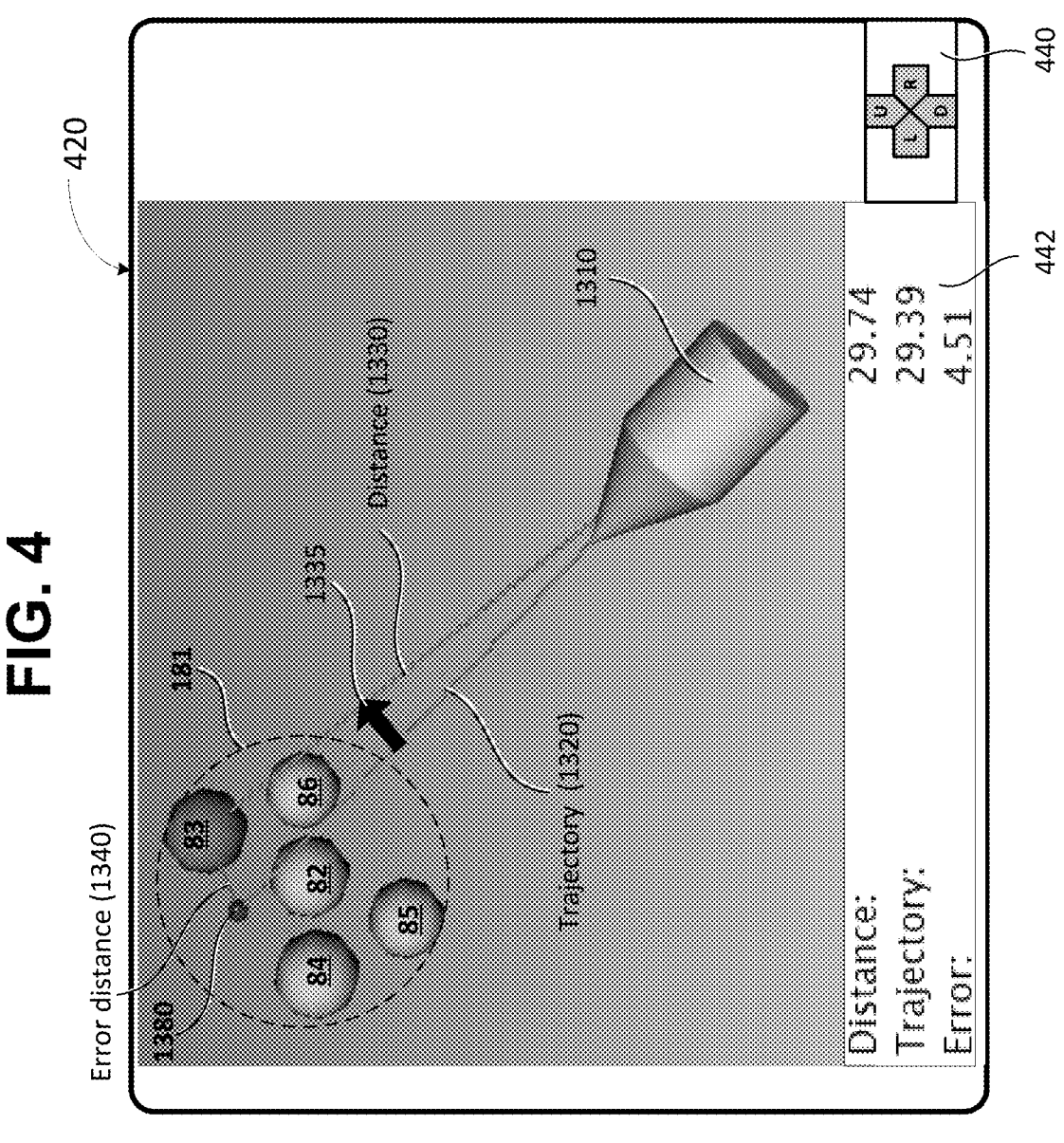
FIG. 4 shows measurements displayed to the user in a display screen indicating a deviation between the catheter trajectory and a selected satellite target.
Figure 5A:
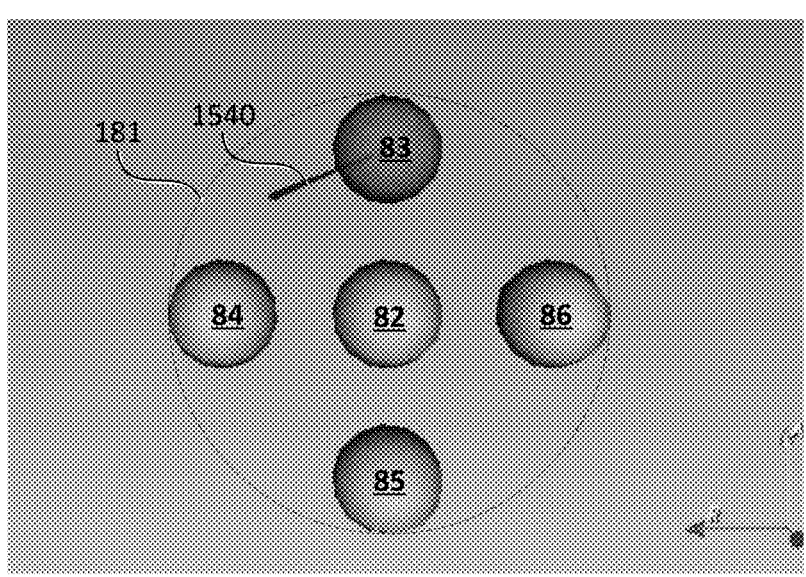
FIG. 5A shows a display screen displaying the direction in which the user needs to move the catheter tip to align the catheter tip with a selected satellite target.
Figure 5B:
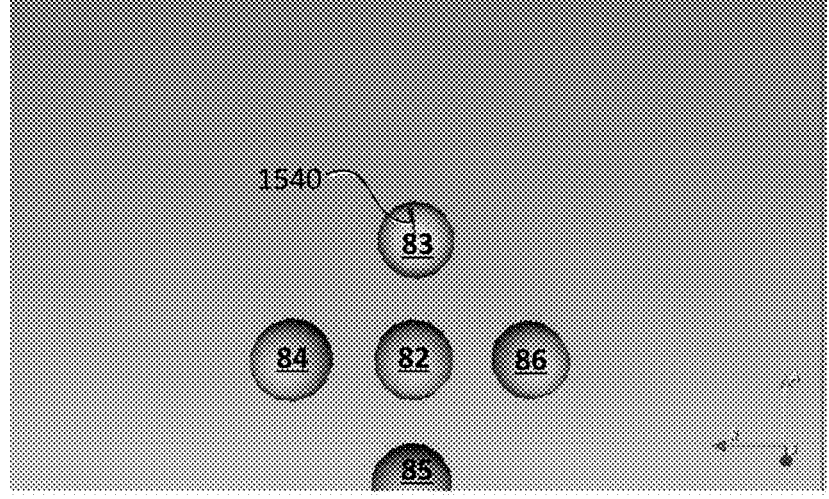
FIG. 5B shows the display screen indicating when the catheter tip is aligned with the satellite target.

FIG. 4, FIG. 5A, and FIG. 5B illustrate examples of robot-assisted catheter alignment and/or navigation. As described above, catheter 110 is initially inserted in a patient 80 (e.g., a natural orifice or small incision), and kinematically navigated through a lumen 81 to a region of interest (lesion 81). The user aligns the catheter tip with a main target using the live-view image of the endoscope camera. Thereafter, user removes the camera and inserts an interventional tool. The system guides the user to align and/or navigate the catheter tip to a plurality of satellite targets surrounding the main target. FIG. 4 shows a display screen 420 of the computer system 400 indicating one possible arrangement of a catheter tip 1310 with respect to a plurality of targets within a lesion 181 which is a region of interest. The display screen 420 can display the catheter tip 1310 and the lesion 181, along with a graphical user interface (GUI) 440 and a measurements section 442. Specifically, FIG. 4 shows a reference target 82 surrounded by a first satellite target 83, a second satellite target 84, a third satellite target 85, and a fourth satellite target 86. Here, the user has selected the first satellite target 83 to be aligned with the catheter tip 1310. The arrangement of the reference target 82 and satellite targets 83-86 in real-space can be considered in a two-dimensional (2D) plane (e.g., targets can be substantially at a same depth from the catheter tip) or in a three-dimensional (3D) environment (e.g., targets can be at different depths or different planes from the catheter tip). Therefore, the trajectory 1320 from the catheter tip 1310 to the reference target 82, and the actual distance from the catheter tip to each of the satellite targets 83-86 must be accurately determined prior to aligning and navigating the catheter tip 1310 to each satellite target.

In FIG. 4, the measurements display section 442 informs the user of a deviation between the catheter trajectory 1320 and the selected (active) satellite target 83. One way that the software system can assist the user in correcting the deviation and accurately aligning the catheter tip 1310 to the satellite targets is by providing instructions in a virtual view of the procedural environment, based on the real-time positional relation between the catheter tip 1310 and the selected satellite target. For example, as shown in FIG. 4, the software system can generate and display lines (trajectory, distance, error, etc.) and arrows 1335 to instruct the user on the direction needed to bend the catheter to improve the alignment of the catheter tip 1310 with each satellite target. The direction of the arrow or arrows 1335 should ideally match with the direction in which the user should move the joystick of a controller to actuate the steerable section of the catheter. To that end, the software system can be programmed to measure the deviation from the tool trajectory 1320 to the target, and display these values to the user along with instructions for making appropriate adjustments. For example, the software system can calculate the angle in which the catheter body needs to be bent, as well as the absolute distance 1330, the actual trajectory distance 1320, and the real-time miss distance (i.e., the real-time "error distance" 1340) for proper alignment.

In FIG. 4, the measurements display section 442 shows real-time values for absolute distance 1330, the current trajectory 1320, and the error distance 1340 between the catheter tip 1310 and the selected satellite target 83. The absolute distance 1330 is the real-time distance in 3D space from the catheter tip 1310 to the selected target. The trajectory 1320 is the distance from the catheter tip 1310 to the plane containing the selected target 83 (i.e., the distance from the catheter tip to the plane which is perpendicular to the catheter axis and which passes through the center of the selected satellite target). A point 1380 represents an intersection of the catheter trajectory 1320 with the plane which passes through the center of the selected satellite target 83. The catheter trajectory 1320 can also represent the insertion depth that the physician needs to insert the tool (e.g., an ablation tool) to reach the center of the lesion or satellite position thereof. The miss distance (or error distance 1340) indicates how far off the trajectory 1320 is from the selected satellite target 83. In this embodiment, the software system is configured to enable the user to minimize the miss distance to substantially zero or to within a minimum threshold value based on the size of the lesion. This "error distance" information can be used by the user to manually steer the catheter, for example, by using a graphical user interface (GUI) 440 provided in the display screen 420. Alternatively, or in addition, this "error distance" information can be sent directly to the system controller to autonomously control the catheter alignment with the selected satellite target. When the actuation of the catheter is controlled autonomously, the software system can control the alignment of the catheter tip iteratively and provide a prompt to the user to confirm if the calculated trajectory is satisfactory to reach the desired or selected target location.

In one or more embodiments, the size and shape of each satellite target can be defined manually or automatically, for example, based on the size of the lesion and number of targets. The "size", "shape", "volume" or similar parameter of the satellite targets here represents the region of an anatomy in which the user should be targeting, with a certain margin of error. The region can be defined in either two-dimensional (2D) or three-dimensional (3D) shape, and each satellite target can have the same or different shape as another. The margin of error can be defined manually or automatically. The margin of error (tolerance) can be a fixed value or a percentage of the region. In one or more embodiments, the margin of error can be a unique value for each satellite target, or a uniform value (e.g., a percentage of the size of the lesion) applied to all targets at once.

FIG. 5A and FIG. 5B show the direction in which the user needs to move the catheter to align the catheter trajectory with the selected satellite target. Advantageously, when the catheter is correctly aligned with the selected satellite target, the software system can provide an indication of when the catheter is aligned with the selected satellite target. Alternatively, if the software system determines that the catheter is not aiming at the area within the satellite target and the error margin is greater than a predetermined threshold, the software can provide a warning alert the user to avoid sampling. Similarly, when the satellite target is within the margin of error, the software system can provide a confirmation alert so that the user can begin sampling. This warning or confirmation alerts can be provided by audible, visual, haptic or other known techniques. One example of a visual alert is to have the attributes of the selected satellite target change, either discretely or continuously, based on the distance that the trajectory is from intersecting the selected satellite target.

In one implementation, shown in FIG. 5A and FIG. 5B, the software system displays a reference target 82 and a plurality of satellite targets including a first satellite target 83, a second satellite target 84, a third satellite target 85, and a fourth satellite target 86, within a lesion 181 which is a region of interest. In FIG. 5A, the software system assigns a first color (e.g., RED) to the first satellite target 83 when the actual trajectory (not shown) of the catheter is not intersecting the selected satellite target 83. In FIG. 5B, the software system assigns a second color (e.g., GREEN) to the selected satellite target 83 when the actual trajectory of the catheter is intersecting the satellite target 83. In addition, the software system also displays navigation and targeting data. For example, the system displays directional arrows and numerical values indicative of the manner in which the user should control the steerable sections of the catheter sheath. In FIG. 5A, the selected satellite target 83 turns red when the catheter trajectory is misaligned with the selected (active) satellite. In addition, a line indicator 1540 is also drawn from the virtual center of the catheter to the center of the satellite target 83. The line indicator 1540 is displayed in manner which is indicative of the magnitude and direction in which the catheter needs to be bent to improve the alignment. In FIG. 5B, the satellite target 83 turns green (a different color) when the trajectory of catheter is aligned with the selected target. In FIG. 2, the line indicator 1540 connecting the catheter to the center of the satellite target 83 is still shown to direct the user to improve the alignment even more. To inform the user that the catheter is being aligned with the desired target, the magnitude (length or size) of the line indicator 1540 is reduced as the trajectory of the catheter becomes more accurately aligned with the satellite target.

<Placement of Satellite Targets>

According to one or more embodiments, an implementation for the placement of satellite targets is that the software system is configured (programmed) to automatically place satellite targets within a desired distance relative to the reference target. The reference target is usually designated as the center of the segmented lesion (or a region of interest). Therefore, satellite targets can be automatically arranged near the reference target according to certain criteria. For example, satellite targets can be arranged at predetermined distances from the center of the lesion, and/or the satellite targets can be distributed in a predetermined pattern (e.g., in a circular pattern at predetermined number of degrees or in an a elliptical pattern, on in any other geometrical pattern in 2D or 3D space). The criteria for defining satellite targets may depend on the type of interventional procedure to be performed through the endoscope or catheter (steerable catheter 110). There is no limit to the number or forms of arrangement of satellite targets and such arrangement can be set manually by the user or automatically by the system. Furthermore, while it can be advantageous to define and arrange satellite targets during intra-operative procedures (e.g., by first visually confirming the position and orientation of the reference target), in at least some embodiments, the reference target and the satellite targets can be defined prior to catheter insertion (e.g., based on pre-operative images).

Automatic placement (arrangement) of the satellite targets can be based on a simple pre-set pattern, or it can be based on other parameters, like the size and/or homogeneity of the lesion. Automatic placement can also be based on parameters such as the size of the end effector, or of the type of tool to be used in a given interventional procedure. For example, for a biopsy procedure, the size and/or number of satellite targets to be sampled can be different than the number of satellite targets for an ablation procedure to treat a lesion or tumor. The distribution and location of the satellite targets with respect to the reference target can also be set manually by the user based on the user's knowledge and expertise. In some embodiments, a fourth dimension such as time of a biological cycle of the patient can be added to the arrangement of the satellite targets. For example, the satellite targets can be arranged at specific positions and/or orientations with respect to the reference target depending on the heartbeat cycle, respiratory cycle, blood flow, airflow, blood pressure, or other biological parameter of the patient. In other words, when considering a biological parameter of a patient (e.g., a respiratory cycle), a satellite target can be defined to be aligned with the catheter tip only at a predetermined phase of the biological parameter (e.g., at full inhale or full exhale of the respiratory cycle).

Figure 6A:
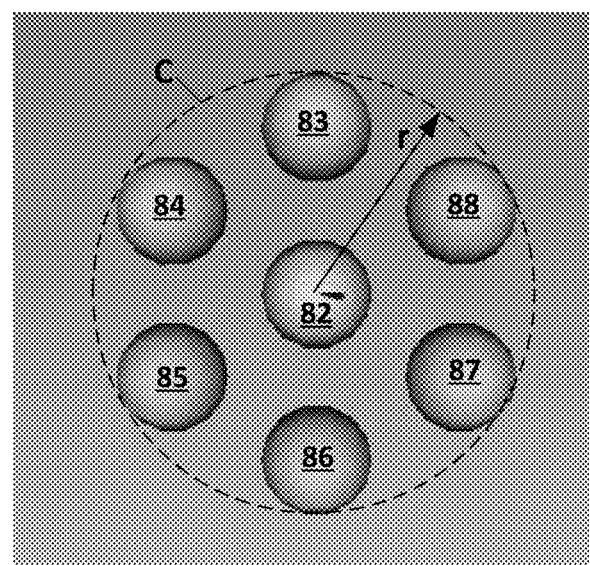
FIG. 6A, FIG. 6B and FIG. 6C show a display screen with examples of placement of satellite targets around a main (reference) target.
Figure 6B:
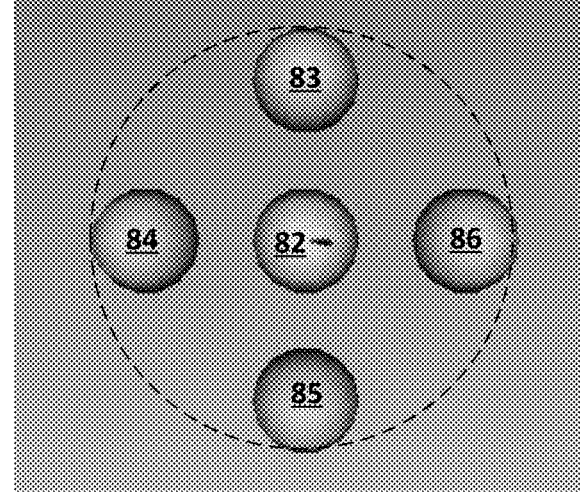
Figure 6C:
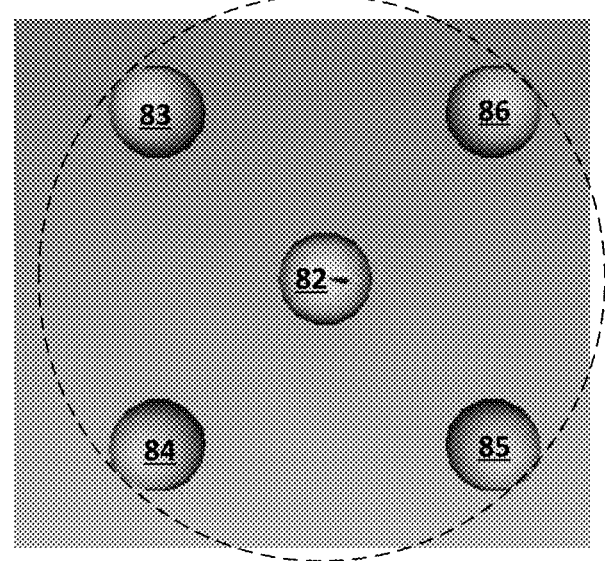

FIG. 6A, FIG. 6B and FIG. 6C show examples of automatic satellite target placement. In one implementation, shown in FIG. 6A, FIG. 6B, and/or FIG. 6C, the software distributes the satellite targets in a circle on a 2D plane, with the reference target in the center of the circle. The 2D plane is based on the orientation of the catheter, and the satellite targets are placed substantially equally distant around the circumference of this circle based on the number of satellite targets. The orientation and radius of this circle can be adjusted manually or automatically, for example, based on the size of the lesion (e.g., tumor). This distribution can also be in any shape or pattern, and the arrangement can be 2D or 3D. The software automatically distributes the satellite targets in a circle around the reference (center) target on the 2D plane perpendicular to the catheter trajectory.

FIG. 6A shows automatic distribution of six satellite targets around a reference target 82. Specifically, the system has arranged a first satellite target 83, a second satellite target 84, a third satellite target 85, a fourth satellite target 86, a fifth satellite target 87, and a sixth satellite target 88 around a reference target 82. In this arrangement, the satellite targets are spaced apart by 60 degrees from each other around a circle (C) of radius (r), and equidistantly from the reference target 82. FIG. 6B shows automatic distribution of four satellite targets (83, 84, 85 and 86) which are spaced 90 degrees apart from each other, and equidistantly from the reference target 82. FIG. 6C shows automatic distribution of four satellite targets spaced 90 degrees apart, similar to FIG. 6B. However, in FIG. 6C, the orientation is of the satellite targets is rotated 90 degrees with respect to the arrangement of FIG. 6B, and the radius (r) of circle C is increased. As noted above, the arrangement is not limited to any specific geometric shape or number of satellite targets. As long as at least one satellite target (one or more satellite targets) is defined and arranged at a desired (predetermined) distance with respect to the reference target, the system can advantageously display virtual representation of the distal portion of the catheter, and a virtual representation of the satellite target, and this information (navigation guidance) should be enough for a user to be able to determine how to align/navigate the catheter tip with/to the one or more satellite targets.

<Satellite Targets Identification and Labeling>

Figure 7A:
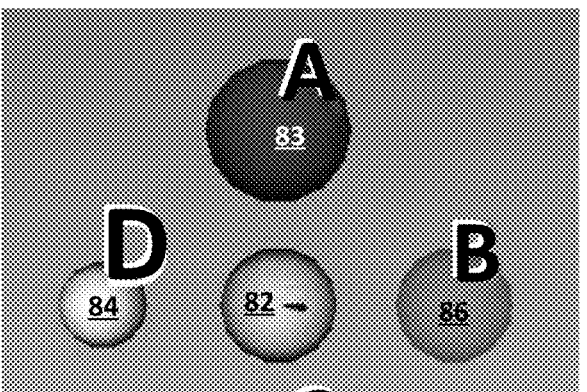
FIG. 7A shows how each satellite target can be generated and labelled to have a unique appearance.
Figure 7B:
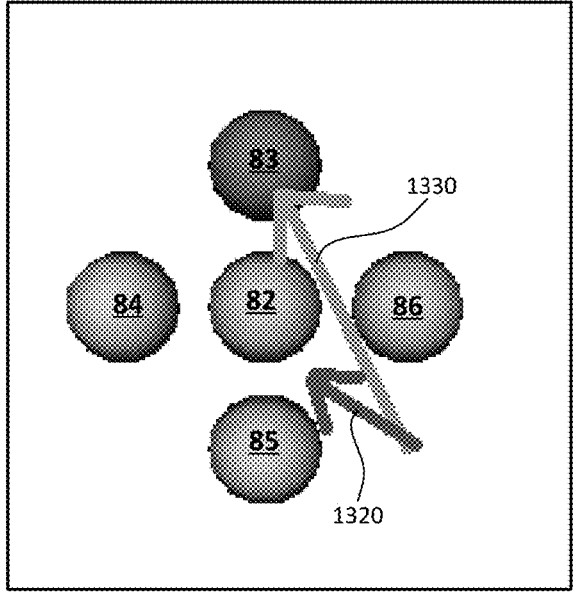
FIG. 7B shows an embodiment where the system displays directional arrows to provide navigational guidance for aligning and guiding the catheter tip to satellite targets.
Figure 7C:
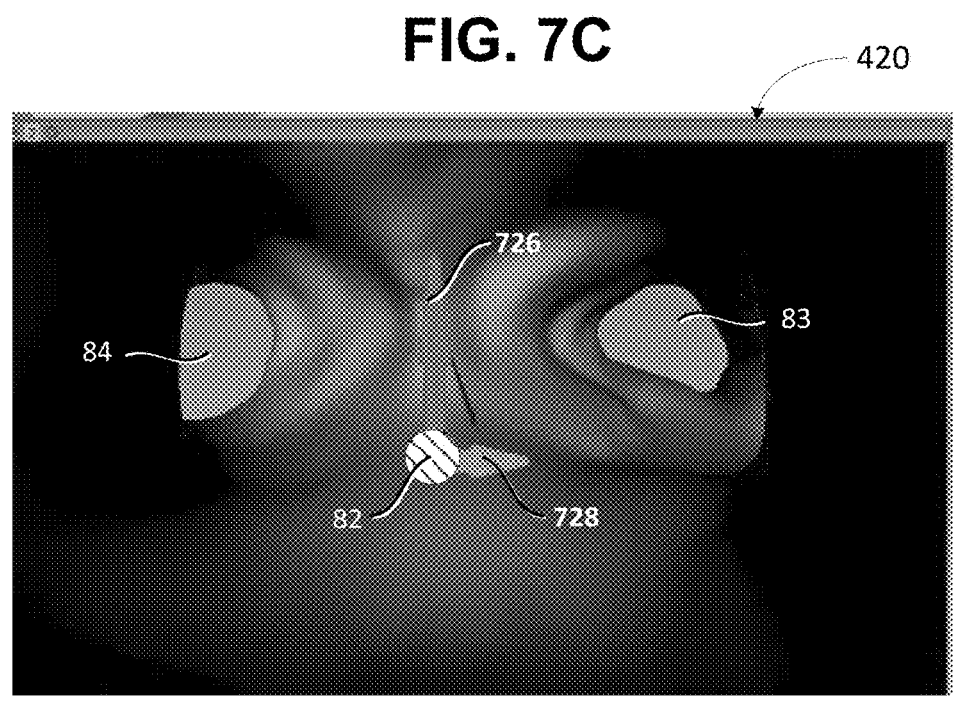
FIG. 7C shows an embodiment where the system generates a virtual first-person view (FPV) of a patient's anatomy and uses satellite targets for successively navigating the catheter tip to different locations of the patient's anatomy.

Satellite targets can be categorized to have unique shapes, identification (ID), and/or procedure application. In other words, although satellite targets can have a unique advantage in assisting a user to navigate to neighboring locations surrounding the center of a lesion, satellite targets may also be used in assisting the user to navigate neighboring organs of an anatomical region. FIG. 7A shows how each satellite target can be labelled and designated to have a unique appearance when defining multiple targets within a region of interest. FIG. 7B shows an embodiment where directional arrows are used to provide navigational guidance for guiding the catheter tip to satellite targets. FIG. 7C shows a simulated first-person view (FPV) for navigating the catheter tip from a reference target location within a lumen to neighboring (satellite) locations of a patient anatomy.

More specifically, according to at least one embodiment, each individual target can be identified and tagged with a unique name (ID), number, color, shape, etc. This identification can be done automatically by the software or manually by the user. An example of identifying satellite targets is shown in FIG. 7A. In FIG. 7A, the center target is defined as a reference target 82, and is assigned a first color (GREEN). In contrast, the satellite targets are identified by a different color, different name or ID (A, B, C, D), and defined by a different size. For example, the first satellite target 83 is tagged by a letter "A", assigned a color (Blue), and defined by a circular or spherical shape of the largest diameter among satellite targets. The second satellite target 84 is tagged by a letter "B", assigned a color (white), and defined by a spherical or circular shape having the smallest diameter among the satellite targets. Similarly the third satellite target 85 and fourth satellite target 86 are respectively tagged by letters "D" and "C", assigned different colors (yellow and purple respectively), and both have diameters of different size than the first and second satellite targets. In at least some embodiments, the system or user can also selectively hide or show each satellite target individually. For example, to keep track of which targets have already been imaged and/or sampled, the system can mark each processed target, by fading or hiding it entirely from view (i.e., the system suppresses or prevents display of the target already processed). In this manner, the system can control display of the satellite targets for intra or post procedure reference. Here, the size or shape of the satellite targets can be indicative of the volume or area to be treated. For example, in FIG. 7A, the size of each satellite target can be indicative of the size of ablation to be performed. In that regard, the user can be informed to use an amount of ablative energy according to the size of each satellite target.

FIG. 7B shows another example of defining satellite targets (S316) and proving navigation guidance to the user (S322). In FIG. 7B, the image of the reference target and satellite targets includes two arrows, where a first arrow 1320 (blue arrow) represents the direction and magnitude to bend the tip of the catheter, and a second arrow 1330 (green arrow) represents the direction and magnitude to move the middle section 102 of the steerable catheter 110 to reach a selected (active) satellite target 83. Adjusting the aiming of the distal tip 1310 to align and guide the catheter to a satellite target may also be applicable to guiding the tip of the catheter beyond a bifurcation of a biological lumen to reach an additional target or a bifurcated branch of the lumen.

FIG. 7C illustrates an exemplary use of a main (reference) target and satellite targets for advancing the catheter tip in a first-person view (FPV) from a main lumen to one or more secondary lumens. In this example of FIG. 7C, similar to the previous embodiments, the catheter tip may be guided using the endoscope camera live-view image to a predetermined reference target along a lumen. Once the catheter is navigated to, and aligned with, a reference target 82, the user may remove the camera. Thereafter, after swapping the camera for a tool, the system may use a virtual image of secondary lumens to navigate the distal tip of the catheter to a satellite target. In FIG. 7C, the initial or reference target 82 can be the carina of an airway (lumen 81), and the satellite targets (first satellite target 83 and second satellite target 84) correspond the bifurcations from the carina. In this case, the reference and satellite targets are not necessarily "lesions" within a region of interest. Instead, the region of interest includes targeted lumens where an interventional procedure can be carried out. Therefore, the tip of the catheter (not shown in FIG. 7C) can be guided in the FPV by a first arrow 728 and a second arrow 726. In this example, the first arrow 728 can indicate the direction and magnitude for maneuvering the catheter tip (distal portion), and the second arrow 726 can indicate the direction and magnitude for maneuvering the middle section of the catheter in order to reach a satellite target 83 (e.g., the right-hand bifurcation of the carina in the airway of a patient). It will be appreciated that guiding the catheter tip to the first carina (reference target 82) using the live-view image of the endoscope camera, and thereafter guiding the catheter tip or an interventional tool to the branches of the carina (satellite targets) aided by the arrows 726-728 (guidance information), ensures fast and accurate delivery of the catheter to the region of interest.

In any case, it is advantageous to define a reference target and one or more satellite targets identified by unique parameters. A unique identification for each satellite target can be useful if the catheter orientation changes (or needs to be changed) to keep track of which targets have already been imaged and/or sampled. Previously sampled satellite targets can also be marked in a certain unique manner, for example, by fading or hiding it entirely from view. The physician can also map the unique identification of the virtual satellite target to the physical sample.

In any of the foregoing embodiments and examples, the arrangement of the satellite targets can be entirely manual done by the user or can be automated based on known algorithms. In that regard, a method of providing navigation guidance to perform an intraluminal procedure in a patient's body, comprises: navigating the distal portion of the steerable catheter 110 into the patient's body by transmitting an actuating force from an actuator unit connected to a proximal portion of the steerable catheter and advancing the distal portion thereof through a lumen of the patient's body; recording, using a tracking system connected to the computer system, a positional relation between the distal portion of the catheter and a reference target located in a region of interest near the catheter tip; receiving, through the user interface, inputs regarding one or more satellite target locations to be arranged surrounding the reference target within the region of interest; calculating, by the processor, one or more trajectories for aligning the distal portion of the catheter to each one of the one or more satellite targets, and displaying, on the display screen (420), one or more of the following: (a) a virtual representation of the distal portion of the catheter, (b) an image of the reference target, (c) a virtual representation of the one or more satellite targets, and (d) navigation guidance for successively guiding the distal portion of the catheter to each of the one or more satellite targets.

<Software Related Disclosure>

At least certain aspects of the exemplary embodiments described herein can be realized by a computer system 400 or apparatus that reads out and executes computer executable instructions (e.g., one or more programs or executable code) recorded on a storage medium (which may also be referred to as a 'non-transitory computer-readable storage medium') to perform functions of one or more block diagrams or flowchart diagrams described above. The computer may include various components known to a person having ordinary skill in the art. For example, the computer may include signal processor implemented by one or more circuits (e.g., a field programmable gate array (FPGA) or an application specific integrated circuit (ASIC)) for performing the functions of one or more of the above-described embodiment(s), by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)), and may include a network of separate computers or separate processors to read out and execute the computer executable instructions. The computer executable instructions may be provided to the computer, for example, from a cloud-based network or from the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. The computer may include an input/output (I/O) interface to receive and/or send communication signals (data) to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

MODIFICATIONS AND OTHER EMBODIMENTS

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

According to one or more embodiment disclosed herein, the system can allow the user to create sub-targets or satellite targets surrounding a reference target or center of a lesion.

Advantageously, the system can be configured to assist on the creation and even distribution of these sub-targets with modifiable patterns or individual placement. The system or the user can identify each satellite target with a unique ID, name, color, shape, etc., for intra or post procedure reference. The software system automatically displays measurements, like orientation angle, distance error, insertion trajectory, and insertion depth for guiding a tool (e.g., a biopsy needle) from the distal tip of the catheter sheath to the satellite targets. The software is configured to indicate (confirm) to user when a trajectory falls within the desired region, and to warn when a trajectory is not within a threshold margin. In most embodiments, either the software or the user can cycle through each satellite target selectively. The software is configured to update the measurements, alignment, and status (active or non-active) of the catheter with respect to the targets, and to provide indications accordingly.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A robotic system for an intraluminal procedure, the robotic system comprising:

a catheter having a proximal portion attachable to an actuator unit and a distal portion insertable into a lumen;

a tracking system including at least one sensor, the tracking system configured to record position and orientation of the distal portion of the catheter; and a processor in communication with the actuator unit and the tracking system, the processor being configured to:

register, in a navigation mode, at least one of the recorded position and orientation of the distal portion of the catheter with respect to a reference target;

generate, in a targeting mode, at least two satellite targets;

generate, in the targeting mode, a virtual representation of the distal portion of the catheter and a virtual representation of the at least two satellite targets;

control displaying the virtual representation of the at least two satellite targets, and generate, in the targeting mode, actions to align a tip of the catheter with a selected target, wherein the processor is further configured to:

control displaying one or more of a distance error, an insertion trajectory, and an insertion depth for aligning and/or navigating the distal end of the catheter to at least one of the at least two satellite targets, and modify size, suppress, or fade the display of the virtual representation of the at least one of the at least two satellite targets based on information regarding the intraluminal procedure performed on a selected at least one of the at least two satellite targets.

2. The robotic system according to claim 1, wherein the processor is further configured to:

generate a virtual representation of the reference target;

calculate, based on the position and/or orientation of the distal portion of the catheter, subsequent positions and/or orientations for the distal portion of the catheter to successively align and/or navigate the distal portion of the catheter to each one of the satellite targets; and control displaying the virtual representation of the reference target and a plurality of arrows representing at least one of direction and magnitude for at least one of bending the distal portion of the catheter, and moving the catheter to navigate to a selected satellite target.

3. The robotic system according to claim 1, wherein the processor is further configured to control displaying one or more of: a recorded image of the reference target, the virtual representation of the distal portion of the catheter and a virtual representation of the reference target, and wherein the displaying aids successive aligning and/or navigating of the distal portion of the catheter with the at least two satellite targets.

4. The robotic system according to claim 1, wherein:

the processor is further configured to prompt a user to successively select each of the at least two satellite targets to which the distal portion of the catheter is to be aligned and/or navigated.

5. The robotic system according to claim 1, wherein the processor is further configured to control displaying an orientation angle for aligning and/or navigating the distal end of the catheter to at least one of the at least two satellite targets.

6. The robotic system according to claim 5, wherein the processor is further configured to:

update the one or more of the orientation angle, the distance error, the insertion trajectory, and the insertion depth, and output navigation guidance showing a user how to successively align the distal portion of the catheter with at least one of the at least two satellite targets.

7. The robotic system according to claim 1, wherein:

the catheter includes a tool channel with a removable imaging device at a distal end thereof, and after registering the position and/or orientation of the distal portion of the catheter with respect to the reference target, the processor is further configured to prompt a user to remove the imaging device from the tool channel and insert an end effector tool through the tool channel without removing the catheter from the lumen.

8. The robotic system according to claim 7, wherein the processor is further configured to control display of an orientation angle for guiding the end effector tool from the distal portion of the catheter to at least one of the at least two satellite targets.

9. The robotic system according to claim 8, wherein the processor is further configured to control:

when the insertion trajectory intersects a selected one of the at least two satellite targets to within a threshold value, output of a confirmation, and when the insertion trajectory does not intersect the selected one of the at least two satellite targets by a distance error greater than the threshold value, output of a warning.

10. The robotic system according to claim 8, wherein the processor is further configured to prompt the user to cycle through each of the at least two satellite targets to perform the intraluminal procedure utilizing the end effector tool on each one of the at least two satellite targets.

11. The robotic system according to claim 1, wherein the processor is further configured to control a size of the virtual representation of the at least two satellite targets, and wherein display size of each satellite target is based on a total number of the at least two satellite targets.

12. The robotic system of claim 1, wherein the actions to align the tip of the catheter with the selected target include providing instructions in a virtual view based on a real-time positional relation between the catheter tip and the selected target.

13. A method of providing navigation guidance for an intraluminal procedure, the method comprising:

introducing a distal portion of a catheter into a lumen of a patient;

recording a positional relation between the distal portion of catheter and a reference target;

determining, based on the recorded positional relation, a position and/or orientation of the distal portion of the catheter with respect to the reference target;

generating at least two satellite targets around the reference target;

generating a virtual representation of the distal portion of the catheter and a virtual representation of the at least two satellite targets; and displaying one or more of a distance error, an insertion trajectory, and an insertion depth for aligning and/or navigating the distal end of the catheter to at least one of the at least two satellite targets, wherein display size of each satellite target is based on a total number of the at least two satellite targets.

14. The method according to claim 13, further comprising:

generating a virtual representation of the reference target;

calculating, based on the position and/or orientation of the distal portion of the catheter, subsequent positions and/or orientations for the distal portion of the catheter to successively align and/or navigate the distal portion of the catheter to each of the at least two satellite targets; and displaying the virtual representation of the reference target, the virtual representation of the at least two satellite targets, and a plurality of arrows representing at least one of direction and magnitude for at least one of bending the distal portion of the catheter and moving the catheter to navigate to a selected satellite target.

15. The method according to claim 13, wherein the catheter includes a tool channel with a removable imaging device at a distal end thereof, the method further comprising:

prompting a user to remove the imaging device from the tool channel and to insert an end effector tool through the tool channel without removing the catheter from the lumen.

16. The method according to claim 15, further comprising:

displaying, on a display screen, an orientation angle for guiding the end effector tool from the distal portion of the catheter to at least one of the at least two satellite targets.

17. The method according to claim 15, further comprising:

displaying, on a display screen, one of a confirmation and a warning, wherein the confirmation is displayed when the insertion trajectory of the end effector tool intersects a selected one of the at least two satellite targets to within a threshold value, and wherein the warning is displayed when the insertion trajectory of the end effector tool does not intersect a selected one of the at least two satellite targets by an error distance greater than the threshold value.

18. The method according to claim 13, further comprising:

prompting a user to successively select each of the at least two satellite targets to which the distal portion of the catheter is to be aligned and/or navigated.

19. The method according to claim 13, wherein the virtual representation of the at least two satellite targets is a modifiable pattern.

20. A method of providing navigation guidance to perform an intraluminal procedure, the method executed by a computer system comprising a processor and a graphical user interface, the method comprising:

inserting a distal portion of a catheter into a lumen;

aligning the distal portion of the catheter with a region of interest located inside the lumen;

recording a real-time positional relation between the distal end of the catheter and a reference target;

determining, based on the positional relation, a position and/or orientation of the distal portion of the catheter with respect to the reference target;

generating at least two satellite targets;

calculating, by the processor, a trajectory from the distal end of the catheter to each one of the at least two satellite targets;

displaying an image of the reference target and a virtual representation of the one or more satellite targets;

receiving, through the graphical user interface, at least one input for arranging at least one of the at least two satellite targets around the reference target within the region of interest; and displaying image guidance for successively aligning the distal portion of the catheter with each of the at least two satellite targets, wherein the display size of each satellite target is based on a total number of the at least two satellite targets.

21. The method of claim 20, wherein the image guidance is based on the recorded real-time positional relation and includes changing at least one of a color, a unique identification, a pattern, visibility, and a magnitude of a line indicator.

* * * * *